United States Patent [19]

Shuman

[11] Patent Number: 5,250,660
[45] Date of Patent: Oct. 5, 1993

[54] PEPTIDE PURIFICATION PROCESS

[75] Inventor: Robert T. Shuman, Greenwood, Ind.

[73] Assignee: Eli Lilly and Company, Indianapolis, Ind.

[21] Appl. No.: 790,884

[22] Filed: Nov. 12, 1991

[51] Int. Cl.$^5$ .................. A61K 37/02; C07K 5/00
[52] U.S. Cl. ..................... 530/344; 530/331
[58] Field of Search .............. 530/331, 344; 514/18

[56] References Cited

U.S. PATENT DOCUMENTS

| | | | |
|---|---|---|---|
| 4,377,482 | 3/1983 | Rivier | 530/344 |
| 4,399,065 | 8/1983 | Bajusz et al. | 530/331 |
| 4,533,494 | 8/1985 | Uchiyama et al. | 530/344 |

OTHER PUBLICATIONS

Tomeri et al. Chromatographia, vol. 19 (1984) 437-442.

*Primary Examiner*—Merrell C. Cashion, Jr.
*Assistant Examiner*—Bennett Celsa
*Attorney, Agent, or Firm*—David E. Boone; Leroy Whitaker

[57] ABSTRACT

Tripeptides, D-Phe-L-Pro-L-Arg-H, D-Phg-L-Pro-L-Arg-H and related compounds are purified in a process comprising 1) HPLC chromatography over an alkylsilane resin and elution with a gradient comprising an organic phase of between about 2% and about 40% of acetonitrile in an aqueous acidic phase containing an inorganic acid e.g. $H_2SO_4$ and HCl, at a pH between about 2 and about 3, and 2) adjusting the pH of the acidic eluate with a water insoluble basic ion-exchange resin to about 4 to about 6.5. The purified peptides are useful antithrombotic agents.

8 Claims, No Drawings

PEPTIDE PURIFICATION PROCESS

BACKGROUND OF THE INVENTION

This invention relates to a process for the purification of peptides. In particular it relates to a chromatographic process for the preparative purification and formation of salts formed with inorganic acids of D-phenylalanyl-L-proline-L-arginal and structural variants thereof. The process comprises a preparative purification of the above noted peptides incorporating a salt exchange.

The tripeptide D-Phe-L-Pro-L-Arg-H and related tripeptides are unstable in the free base form owing to their tendency to undergo intramolecular cyclization. These peptides are disclosed by S. Bajusz et al. in U.S. Pat. Nos. 4,703,036 and 4,478,745, while the sulfate salt form of D-Phe-L-Pro-L-Arg-H is described by S. Bajusz et al. in U.S. Pat. No. 4,399,065. Copending application Ser. No. 07/589,553 filed Sep. 28, 1990 describes D-Phg-L-Pro-L-Arg-H and related compounds. These compounds have excellent activity in inhibiting the amidase activity of thrombin, and thus are useful in the prevention and control of the development of blood clots. The preparation of stable salt forms which are pharmaceutically acceptable is an important factor in the therapeutic use of these peptides.

During the preparation of the tripeptide numerous impurities can develop. For example, the formation of D-Phe-L-Pro-D-Arg-H as the incorrect arginine aldehyde isomer can occur. Also the D-Phe or D-Phg group can epimerize to form incorrect isomer and carboxy and hydroxymethyl side products are formed from the arginine portion during preparation. The levels of these undesirable side products are reduced during the process of this invention to acceptable levels.

Reversed Phase High Performance Liquid Chromatography, "RP-HPLC", is widely used in the purification of compounds. Typically, one uses a gradient of an aqueous phase and an organic phase for development of an HPLC chromatogram, for example, aqueous acetic acid or aqueous trifluoroacetic acid for the aqueous phase and an organic solvent or mixture of organic solvents such as acetonitrile, methanol, ethanol or THF. The stationary phase, or column support, may vary but generally an alkylsilane resin is used. In the process provided by this invention the aqueous phase of the gradient comprises an inorganic acid e.g. sulfuric acid or hydrochloric acid, and the peptide product is obtained as the salt formed with the acid. The acidic eluate of the chromatogram is treated with a water insoluble basic resin to neutralize the excess acid in the eluate. Separation of the resin from the eluate by filtration provides a solution of the purified peptide salt essentially free of inorganic salts. The water and acetonitrile are removed from the salt solution by freeze drying or by evaporation to provide the purified peptide salt in solid form.

SUMMARY OF THE INVENTION

A method for the purification of tripeptides represented by the formulae 1 and 2

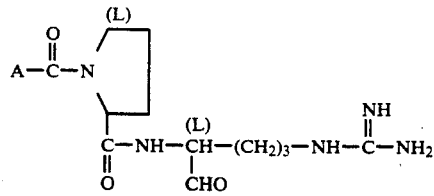

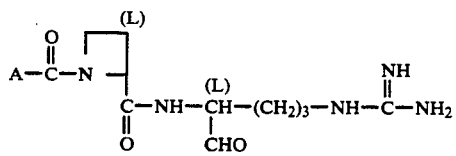

in the form of a salt formed with an inorganic acid is provided. The process comprises chromatographing the impure salt of a compound of the formulae 1 or 2 via reversed phase high performance liquid chromatography by employing a gradient of about 2% to about 40% acetonitrile in an aqueous phase containing an inorganic acid corresponding to the salt form of 1 or 2 at a pH between about 2 and about 3. Following the collection of the salt of 1 or 2 in the eluate, the pH of the eluate is adjusted with a water-insoluble resin in basic form to between about pH 4 to about pH6, filtering the resin and isolating the pure salt by removing the water from the filtrate.

of the formulae 1 and 2 represents the D or DL form of phenylglycine or phenylalanine or an amino or phenyl substituted derivative thereof for example phenylglycyl, N-methylphenylglycyl, N-t-Boc-phenylglycyl, phenylalanyl or N-methylphenylalanyl. Also

represents the R or RS form of an α-alkyl, alkoxy or hydroxy-substituted phenylacetyl group; or a bicyclic group e.g. tetrahydroisoquinolin-1-yl.

Preferred inorganic salts are the sulfates and hydrochlorides of 1 and 2.

DETAILED DESCRIPTION

According to the process of this invention a salt represented by the formulae 1 and 2 in impure form is chromatographed on reversed-phase high performance liquid chromatography wherein the liquid phase comprises a gradient of acetonitrile of from about 2% to about 40% in aqueous acidic phase containing an inorganic acid which corresponds to the salt 1 or 2 at a pH between about 2 and about 3; combining the eluate containing the salt 1 or 2; adjusting the pH of the combined eluate with a water insoluble basic resin to a pH between about 4 and about 6; separating the resin from the eluate and; removing the water from the eluate.

Inorganic acids which can be used in the method include for example, hydrochloric acid, hydrobromic acid, sulfuric acid, and phosphoric acid. Preferred acids are sulfuric acid and hydrochloric acid which provide the sulfate and hydrochloride salts of 1 and 2.

The acid comprises the aqueous phase of the chromatography system. As described above the acid is used at a pH between about 2 and 3. Concentrations of inorganic acids needed to achieve the pH range of the process are very dilute, for example about 0.01% to about 0.05%. Sulfuric acid is preferably used at the lower concentrations of about 0.01% to about 0.02%. Hydrochloric acid preferably is used at a concentration of about 0.04%.

Stationary phase HPLC resins such as the commercially available C18 and C8 reversed phase alkylsilane resins such as Vydac C18 (Pharmacia, Inc.), Spherisorb (Phase Separatons Ltd.), RP Select B (E. M. Merck), and the like, are suitable for use in the process.

As is described above, after the eluate containing the purified salt is collected the pH of the eluate is adjusted to between about 4 and about 6 with a basic resin. Basic resins used are insoluble in the aqueous eluate and are ion-exchange resins in the hydroxide form. Basic resins that can be used in the process include for example, AG1-X8 (Bio-Rad); Dowex 1-X4 (Dow Chemical Co.), IRA 400 (Rohm & Haas, Philadelphia, Pa.). The particular pH to which the eluate is adjusted is dependent on the nature of the peptide, e.g. its structure.

In carry out the method the impure salt represented by the formulae 1 and 2 is dissolved in water or the acidic aqueous phase and the solution loaded on the HPLC column. The gradient of acetonitrile and the acidic aqueous phase is then used to elute the salt. The acid used in the aqueous phase is the acid previously used in the preparation of the impure salt e.g. sulfuric acid is used with crude sulfate salts. Multiple fractions are collected, the number and volume thereof, is not critical. Each fraction is analyzed for the presence of the product 1 or 2 and all fractions containing only the desired product are combined.

The fractions are analyzed by reversed phase HPLC using Fast Protein Liquid Chromatography with a Vydac C18 reversed phase column 0.46×10 cm. The chromatogram is monitored on a Pharmacia UV-M at 214 nM (Pharmacia, Inc., 800 Centennial Ave., Piscataway, N.J. 08854.). The column is eluted with 0.1% aqueous trifluoroacetic acid (A) and 0.1% trifluoroacetic acid in acetonitrile (B) using a gradient of 5-50% B over one hour.

After fractions are combined and the pH adjusted with the basic resin, the resin is separated from the eluate by filtration, centrifugation, decantation or other suitable means. The eluate containing the purified salt is then lyophilized or evaporated in vacuo to provide the purified peptide salt 1 or 2 as a solid. Preferably the eluate is freeze dried.

The peptides purified by the method of this invention are represented by the above formulae 1 and 2 wherein A is 1) a group of the formula $$R-\underset{B}{\overset{R_1}{\underset{|}{C}}}-$$

wherein R is a phenyl group of the formula

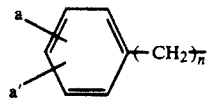

wherein a and a' independently are hydrogen, lower alkyl, lower alkoxy, halogen, trifluoromethyl, hydroxy, hydroxymethyl, amino, or aminomethyl; and n is 0 or 1; or R is thienyl, furyl, naphthyl, or naphthyl mono- or disubstituted by lower alkyl, lower alkoxy, halogen, amino, mono- or di-(lower alkyl)amino, or hydroxy; or R is cyclohexadienyl, cyclohexenyl, cyclohexyl or cyclopentyl;

$R_1$ is hydrogen, methyl or ethyl;

B is lower alkyl, lower alkoxy, hydroxy, or an amino group of the formula $$-N(R_2)(R_3)$$

wherein $R_2$ and $R_3$ independently are hydrogen or lower alkyl, or $R_2$ is hydrogen, and $R_3$ is $C_1$-$C_6$ alkanoyl, halo substituted $C_2$-$C_6$ alkanoyl, or an oxycarbonyl group of the formula $$R_4-OC(O)-$$

wherein $R_4$ is $C_1$-$C_6$ alkyl, $C_2$-$C_6$ alkenyl, $C_3$-$C_7$ cycloalkyl, benzyl, nitrobenzyl, diphenylmethyl, or a phenyl group as defined above; provided, that when $R_1$ is methyl or ethyl, B is other than methyl or ethyl;

2) a bicyclic group of the formula 3

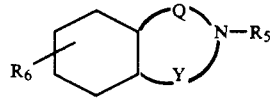

wherein
Q is a one carbon radical represented by

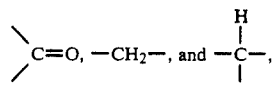

or a two carbon radical represented by

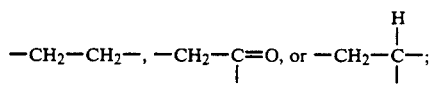

Y is a one carbon radical represented by $-CH_2-$, or

or a two carbon radical represented by

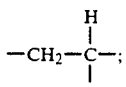

provided that one, but not both, of Q and Y is

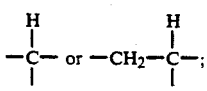

and, provided further, that only one of Q and Y is a two carbon radical;

$R_5$ is hydrogen or an oxycarbonyl group, $R_4$—OC-(O)—, as defined above; and $R_6$ is hydrogen, lower alkyl, lower alkoxy, halogen, hydroxy, trifluoromethyl, carboxy, carbamoyl, or aminosulfonyl; and the dotted circle within the 6-membered ring indicates an aromatic ring or a perhydro ring;
and the salts thereof formed with hydrochloric, hydrobromic, sulfuric and phosphoric acids.

The peptides represented by the formulae 1 and 2 are unstable in the free base form and have improved stability as salts formed with weak organic acids such as acetic acid. The salts formed with inorganic acids, especially sulfuric acid and hydrochloric acid, possess enhanced stability.

The purified salts 1 and 2 provided by the method described herein are antithrombotic agents which inhibit the action of thrombin and the development of blood clots.

The tripeptides and derivatives thereof represented by formulas 1 and 2 are prepared by known methods of peptide coupling as described by Bajusz et al. U.S. Pat. Nos. 4,478,745, and 4,703,036, and 4,399,065.

According to one such method the acid A—COOH, wherein A has the same meanings as defined for formula 1, is coupled with a carboxy protected proline to form the dipeptide (when A is an amino acid) or an N-acylproline ester (when A is other than an amino acid). The carboxy protecting ester group of the proline moiety of the product is removed and the free acid form of the dipeptide is coupled with the lactam form of arginine. The above reaction sequence is illustrated by the following scheme

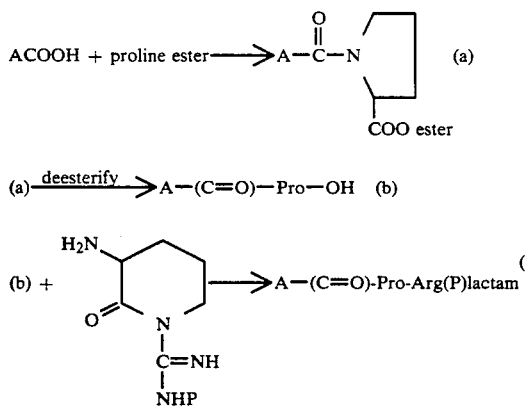

wherein P represents an amino protecting group.

The coupled Arg(P) lactam product (c) is reduced with lithium aluminum hydride in an inert solvent to cleave the lactam ring and provide the tripeptide in the arginine aldehyde form represented by the formula

wherein Arg(P)-H represents amino protected arginine aldehyde.

The lactam form of arginine is obtained by intramolecular coupling of amino protected arginine [Arg-OH]. For example, Boc-Arg(Cbz)OH represented by the formula

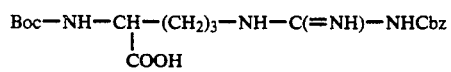

is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of a stronger tertiary amine base such as triethylamine effects the internal acylation to provide the lactam form of the diamino protected arginine as shown below.

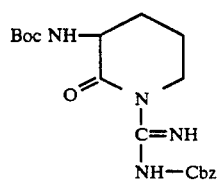

Prior to use in the coupling with the A(C=O)-Pro-OH as shown in the above scheme, the Boc protecting group is selectively removed with trifluoroacetic acid to provide the requisite free amino group.

The coupling of an ACOOH compound with a proline ester, when A is an amino acid residue, is carried out by first protecting the amino group of the amino acid. Conventional amino protecting groups commonly used for temporary protection or blocking of the amino group are employed. Examples of such protecting groups include the alkoxy, alkenyloxy, cycloalkoxy and aryloxycarbonyl groups such as ethoxycarbonyl, t-butyloxycarbonyl, cyclohexyloxycarbonyl, adamantyloxycarbonyl, trichloroethoxycarbonyl, benzyloxycarbonyl, diphenylmethoxycarbonyl, and like groups. The ester group employed to protect the carboxy group of proline during the coupling reaction can be any of the commonly used readily removable ester groups such as t-butyl, benzyl, p-nitrobenzyl, p-methoxybenzyl, diphenylmethyl, trichloroethyl, phenacyl, or trialkylsilyl esters. In carrying out the coupling reaction one employs an ester group for proline which is removable by conditions under which the amino protecting group remains intact. The amino protecting group of the acylating acid ACOOH thus remains in place for protection of the amino group during the subsequent coupling with the arginine lactam compound to form c.

The compounds represented by the formulas 1 and 2 wherein A is the group $(R)(R_1)(B)C$— and B is an amino group —$N(R_2)(R_3)$ wherein $R_2$ is hydrogen and $R_3$ is lower alkyl are prepared with the corresponding compound wherein B is amino by using known alkylation methods. For example, N-methyl-D-phenylglycyl-L-prolyl-L-arginine aldehyde is prepared by reductive alkylation as follows. Cbz protected D-phenylglycine is coupled in DMF with L-proline t-butyl ester using dicyclohexylcarbodiimide (DCC) and hydroxybenzotriazole (HOBt) to form the dipeptide Cbz-D-phenylglycyl-L-proline t-butyl ester. The peptide is hydrogenated in ethyl alcohol over palladium on carbon catalyst to remove the Cbz protecting group, formaldehyde is added to the reduction mixture and the hydrogenation is continued to form N-methyl-D-phenylglycyl-L-proline t-butyl ester. The N-methyl secondary amino group of the phenylglycyl moiety is protected with the Cbz group by reacting the dipeptide t-butyl ester with benzyl chloroformate in THF containing N-methylmorpholine to form N-Cbz-N-methyl-D-phenylglycyl-L-proline t-butyl ester. The t-butyl ester group is removed at room temperature in trifluoroacetic acid containing anisole to provide N-Cbz-N-methyl-D-phenylglycyl-L-proline. The latter dipeptide is then coupled to the Cbz protected Arg lactam and the lactam ring reductively opened to the Arg aldehyde as described above. Both of the Cbz protecting groups of the tripeptide are removed by hydrogenation over Pd/C catalyst to provide N-methyl-D-phenylglycyl-L-prolyl-L-arginine aldehyde.

Compounds represented by the formulas 1 and 2 wherein A is $(R)(R_1)(B)C-$, and R is cyclohexadienyl or cyclohexenyl and B is an alkylamino group, $-N(R_2)(R_3)$ can be prepared by reduction of the imine formed with a lower alkyl aldehyde with sodium cyanoborohydride. Likewise such N-alkylations can be carried out with a lower alkyl iodide and sodium hydride.

The compounds of the formulas 1 and 2 wherein A is a bicyclo group (3) are prepared by the same coupling methods as above. For example the peptide of formula 1 wherein A represents the 1,2,3,4-tetrahydroisoquinolin-1-yl group (formula 3, q = $-CH_2-CH_2-$, $$Y = -\overset{H}{\underset{|}{C}}-, R_5 = R_6 = H)$$

is obtained by acylation of an ester of proline, such as the benzyl ester, with an active derivative of 1,2,3,4-tetrahydro-1-carboxyisoquinoline. Active derivatives that can be used include the acid halides such as the chloride or bromide, the acid azide, as well as active esters and anhydrides such as those formed with the chloroformates as described above. The ring nitrogen of the tetrahydroisoquinoline (formula 3, $R_5=H$) is protected during the acylative coupling. For example an active ester of N Boc-1,2,3-4-tetrahydro-1-carboxy-isoquinoline formed with iso-butyl chloroformate is used in the acylation of the proline ester. The peptide product N-Boc-1,2,3,4-tetrahydroisoquinolin-1-ylcarbonyl-proline ester is deesterified, the free acid converted to an active ester and the latter coupled to the lactam form of arginine. The lactam product is then converted to the aldehyde form as described above to provide the compound of the formula 1 namely, Boc-1,2,3,4-tetrahydroisoquinolin-1-ylcarbonyl-Pro-Arg-H.

The perhydro bicyclo groups represented by the formula 3 are prepared by hydrogenation of either the partially reduced or unsaturated acids by conventional procedures. For example, 1,2,3,4-tetrahydroisoquinoline-1-carboxylic acid is hydrogenated over platinum oxide in a solvent such as ethanol or acetic acid to provide the perhydro(decahydro) isoquinolin-1-carboxylic acid. The perhydro acids are then used as described above in the acylation of a proline ester. Examples of such perhydro derivatives represented by the formula 1 are N-(D-decahydroisoquinolin-1-oyl)-L-prolyl-L-arginine aldehyde and N-(D-decahydroisoquinolin-3-oyl)-L-prolyl-L-arginine aldehyde.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents. Generally anhydrous conditions are used when, in the coupling reaction, an active ester of the acylating acid is used. For example, the cyclic lactam form of arginine (b) is prepared and coupled with an amino protected azetidine-2-carboxylic acid (a) as shown below to provide the dipeptide (c).

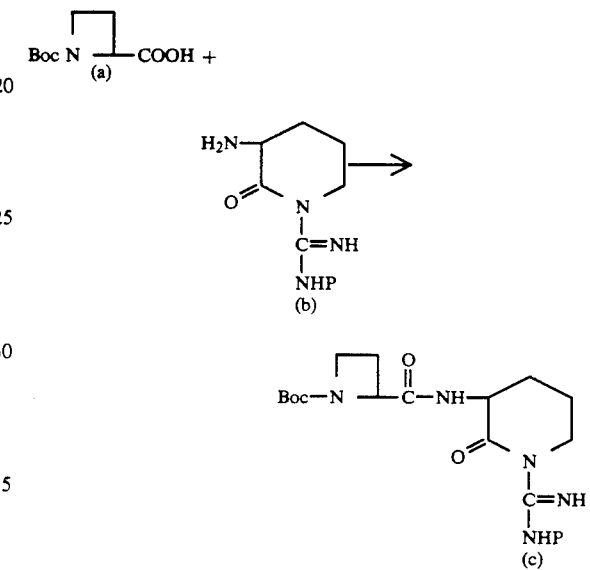

wherein P represents an amino protecting group such as the Cbz group. The Boc, or other suitable protecting group, is removed from the azetidine ring nitrogen which is then acylated with the desired acyl group or amino acid acyl group represented by A(C=O) in the formulas 1 and 2 to provide the tripeptide (d) as shown below.

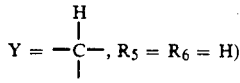

The coupled Arg(P) lactam product (d) is reduced with lithium aluminum hydride in an inert solvent to cleave the lactam ring and provide the tripeptide in the arginine aldehyde form represented by the formula A(C=O)-Azt-Arg(P)-H wherein Arg(P)-H represents amino protected arginine aldehyde.

Preferred embodiments of the invention comprise the preparative purification of compounds represented by the formulas 1 and 2 wherein A is either a bicyclic group represented by the formula 3 or a group (R)(R$_1$)(B)— wherein B is an amino group or amino group substituted by lower alkyl or an oxycarbonyl group and R$_1$ is hydrogen or methyl, which are prepared in the sulfate salt form or the hydrochloride salt form.

The method of the invention provides purified salts (1 and 2) useful for administration as antithrombotic agents. Examples of peptide salts provided by the preferred embodiments are D-1-Tiq-L-Pro-L-Arg-H sulfate, D-1-Tiq-L-Azt-L-Arg-H sulfate, D-Phg-L-Pro-L-Arg-H hydrochloride, Boc-D-Phg-L-Azt-L-Arg-H sulfate, N-methyl-D-Phg-L-Pro-L-Arg-H hydrochloride, Boc-D-Phe-L-Pro-L-Arg-H hydrochloride, N-methyl-D-Phe-L-Pro-L-Arg-H sulfate, Boc-D-Phe-Azt-Arg-H hydrochloride, Boc-D-Phg($\alpha$-CH$_3$)-L-Pro-L-Arg-H sulfate, N-methyl-D-($\alpha$-CH$_3$)Phe-L-Pro-L-Arg-H hydrochloride and sulfate salts; wherein Tiq is 1,2,3,4-tetrahydroisoquinolin-1-yl, Phg is phenylglycyl and Arg-H is arginine aldehyde.

The following Examples are provided to further illustrate the present invention but are not to be considered as limitations thereof.

PREPARATION 1

D-1,2,3,4-Tetrahydroisoquinolin-1-oyl-L-Prolyl-L-Arginine aldehyde Sulfate

To a solution of isoquinoline-1-carboxylic acid (12.5, 0.072 mole) in 185 ml of glacial acetic acid was added 2 g of platinum oxide and the suspension was hydrogenated at room temperature under 60 psi hydrogen pressure in a Parr hydrogenation apparatus for 24 h. The reaction mixture was filtered though a filter pad (Celite) to remove the catalyst and the filtrate was evaporated to dryness in vacuo. The solid residue was triturated with water, filtered and dried to yield 8 g (63% yield) of DL-1,2,3,4-tetrahydroisoquinolin-1-carboxylic acid. FD-Mass spectrum 178 (MH+); $^1$H NMR (DMSO-d$_6$): $\delta$ 2.80-3.00 (m, 3H), 3.15 (m, 1H), 3.30-3.40 (m, 2H), 7.05-7.25 (m, 4H), 7.70 (m, 1H).

The product (7.08 g, 0.04 mole) was dissolved in 2N NaOH (40 ml, 0.08 mole) and 40 ml of t-butyl alcohol and 10.5 g (0.048 mole) of di-tert-butyl dicarbonate were added to the solution. After stirring for 24 h at room temperature the bulk of the t-butyl alcohol was evaporated from the reaction mixture. The resulting aqueous solution was extracted with diethyl ether, the aqueous layer separated and acidified with 2N HCl to pH 2.0. The acidified aqueous phase was extracted with ethyl acetate, the extract dried over MgSO$_4$ and evaporated to dryness in vacuo. The residual oil was dissolved in diethyl ether and 7.9 ml (0.04 mole) of dicyclohexylamine was added to the solution. After standing at 4° C. for 4 h the precipitate of the dicyclohexylamine salt of N-Boc-DL-1,2,3,4-tetrahydro-isoquinolin-1-carboxylic acid was filtered, washed with diethyl ether and dried in vacuo. There were obtained 15.7 g (86% yield) of the pure salt. FD-Mass spectrum 459 (MH+).

Elemental analysis calculated for C$_{27}$H$_{42}$N$_2$O$_4$: Theory: C, 70.71; H, 9.23; N, 6.11. Found: C, 71.07; H, 9.37; N, 5.87.

The Boc protected derivative (73.4 g, 160 mmole) was suspended in 200 ml of ethyl acetate and the suspension was washed with 1.5N citric acid and water, was dried over MgSO$_4$ and evaporated to dryness under vacuum. The residual oil was dissolved in ethyl acetate, the solution cooled to 0° C. and 2,4,5-trichlorophenol (31.6 g, 160 mmole) was added to the solution followed by DCC (33 g, 160 mmole). The reaction mixture was stirred for one hour at 0° C. and at room temperature for 1.5 h. The reaction mixture was cooled to 0° C. the precipitate filtered and the filtrate evaporated to dryness under vacuum. The residual oil was dissolved in 100 ml of pyridine and proline (18.42 g, 160 mmole) and triethylamine (22.3 ml, 160 mmole) were added to the solution. After stirring at room temperature for 24 h. the reaction mixture was evaporated to dryness under vacuum. The residue was dissolved in ethyl acetate, water was added and the pH adjusted to 9.5 with 2N NaOH. The aqueous layer was separated, acidified to pH 2.0 with 2N HCl, and extracted with ethyl acetate. The extract was dried over MgSO$_4$, filtered and evaporated to dryness under vacuum. The oil residue was dissolved in methylene chloride and ethyl acetate. After standing at 4° C. for 4 h a precipitate formed in the solution, was filtered, washed with ethyl acetate and recrystallized from methylene chloride/ethyl acetate. The solid product, Boc-D-1,2,3,4-tetrahydroisoquinolin-1-oyl-L-proline (Boc-D-1-Tiq-Pro-OH), was dried under vacuum to give 19.6 g, 33% yield of the pure product, TLC R$_f$(A) 0.44; FAB-MS, 375 (MH+);

Elemental analysis calculated for C$_{20}$H$_{26}$N$_2$O$_5$; Theory: C, 64.15; H, 7.00; N, 7.48. Found: C, 63.26; H, 6.98; N, 7.52. [$\alpha$]$_D$= +43.14°, C=0.5, methanol.

In a first flask, Boc-D-1-Tiq-Pro (17.8 g, 47.5 mmole) was dissolved in 100 ml of DMF, the solution cooled to −15° C. and 5.3 ml (52.3 mmole) of N-methylmorpholine and 6.2 ml (47.5 mmole) of isobutylchloroformate were added. The mixture was stirred at −15° C. for two min.

In a second flask, the Cbz protected arginine lactam as the trifluoroacetate salt [Arg(Z)-Lactam.TFA], (19.2 g, 47.5 mmole) was dissolved in 40 ml of DMF, the solution cooled to 0° C., and 5.3 ml (52.3 mmole) of N-methylmorpholine were added. The mixture was stirred for 2 min at 0° C. before being added to the first flask. The reaction mixture was stirred for 4 h at −15° C., then was slowly warmed to room temperature overnight and 5 ml of 5% NaHCO3 was added. The reaction mixture was evaporated under vacuum to provide an oil. The oil was dissolved in 175 ml of ethyl acetate and 150 ml of water were added to the solution. The organic layer was separated, washed with 5% NaHCO$_3$, water, 0.1N HCl and with water again before drying over MgSO$_4$. The washed and dried solution was evaporated under vacuum to dryness to yield 24.3 g (79% yield) of the product. Boc-D-1-Tiq-Pro-Arg(Z) lactam, as an amorphous solid.

TLC R$_f$ (A) 0.71. FAB-MS 647 (MH+). [$\alpha$]$_D$= −32.8°, C=0.5 chloroform.

The Arg(Z) lactam product obtained above (23.4 g, 36.2 mmole) was dissolved in 300 ml of dry THF and the solution placed under N$_2$. The solution was cooled to −20° C. and 37 ml lithium aluminum hydride 1M in THF (37 mmole) was added dropwise to the cold solution over 30 min. After addition was completed the mixture was stirred at −20° C. for 30 min, and a solution of 20 ml of THF and 20 ml of 0.5N H₂SO₄ was added dropwise over 10 min. The reaction mixture was diluted with 400 ml of ethyl acetate and 400 ml of water were added. The organic layer was separated, washed twice with 150 ml portions of water and dried over MgSO₄. The washed and dried organic layer was evaporated under vacuum to yield 21 g (89% yield) of the product, Boc-D-1-Tiq-Pro-Arg(Z)-H, as an amorphous solid.

TLC R$_f$(A) 0.28.

The Arg(Z)-H product obtained as described aboved was hydrogenated as follows to remove the Cbz protecting group. The product (18.1 g, 27.9 mmole) was dissolved in 200 ml of THF and 80 ml of water and 28 ml of 1N H₂SO₄ and 3.0 g of 5% Pd-on-carbon were addded. Nitrogen was bubbled through the suspension via a gas dispersion tube for 5 min. followed by hydrogen for 5 h and thereafter nitrogen for 5 min. The catalyst was filtered and the filtrate concentrated to a volume of 100 ml. The concentrate was diluted with 200 ml of n-butanol and the layers separated. The aqueous layer was extracted three times with 100 ml portions of n-butanol and the extracts were combined with the organic layer. The organic layer was evaporated under vacuum, and the reaction product residue triturated with diethyl ether:diisopropyl ether, 1:1, v:v, the solid was filtered and dried under vacuum to give 11.08 g of crude product.

The product was partially purified and obtained as the sulfate salt as follows. The crude product obtained as described above was dissolved in 20 ml of water and 20 ml of 10N H₂SO₄. The solution was heated at 50° C. for 25 min., cooled to room temperature and the pH of the solution was adjusted to 4.0 with Bio-Rad AG1-X8 resin (hydroxide form). The resin was separated from the solution by filtration and the solution was lyophilized to yield 8.44 g of the crude product as the sulfate salt, D-1-Tiq-Pro-Arg-H.H₂SO₄.

EXAMPLE 1

Purification of D-1-Tiq-Pro-Arg-H.H₂SO₄

The sulfate salt (4.2 g) obtained as described in Preparation 1 was dissolved in 0.01% H₂SO₄ and the solution applied to two 5 cm × 25 cm HPLC reversed phase columns (Vydac C₁₈ resin) in series. A gradient of increasing concentrations of acetonitrile (2% to 10%) (aqueous phase=0.01% H₂SO₄) over 10 h was used to elute the product salt. Fractions were collected and pooled on the basis of analytical RP-HPLC profile. The pH of the combined fractions was adjusted to 4.0 using AG1-X8 resin (Bio-Rad analytical anion exchange resin of 50–100 mesh) in the hydroxy cycle. The solution was filtered to remove the resin and the filtrate was lyophilized. There were obtained 2.4 g (57% of theory) of the purified product FAB-MS 415 (MH+). [α]$_D$= −76.12°, C=0.5/0.01N H₂SO₄. Amino acid analysis: Pro, 0.92; Tiq, 1.00. Elemental analysis calculated for C₂₁H₃₂N₆O₇S: Theory: C, 49.21; H, 6.29; N, 16.29; S, 6.26. Found: C, 51.20; H, 6.17; N, 16.88; S, 5.37.

PREPARATION 2

DL-1,2,3,4-tetrahydroisoquinolin-1-oyl-L-azetidinyl-L-arginine aldehyde sulfate

1) DL-1,2,3,4-tetrahydroisoquinolin-1-carboxylic acid

A solution of isoquinoline-1-carboxylic acid (12.5 g, 0.072 mole) in 185 ml of glacial acetic acid was hydrogenated at room temperature for 24 hours over 2 g of platinum oxide catalyst under 60 psi hydrogen pressure in a Parr hydrogenation apparatus. The reaction mixture was filteed through a filter pad (celite) and the filtrate evaporated to dryness in vacuo. The solid residue of product was triturated with water, filtered and dried to give 8 g (63% yield) of pure 1.

FD-MS 178 (MH+)

¹HNMR(DMSO) δ 2.80–3.00 (m, 3H), 3.10–3.20 (m, 1H), 3.30–3.40 (m, 2H), 7.05–7.25 (m, 4H), 7.65–7.75 (m, 1H).

2) t-Butyloxycarbonyl-DL-1,2,3,4-tetrahydroisoquinolin-1-carboxylic acid dicyclohexylamine salt (Boc-DL-Tiq DCHA)

To a solution of 1,2,3,4-tetrahydroisoquinolin-1-carboxylic acid (1) (7.08 g, 0.040 mole) in 2N sodium hydroxide (40 ml, 0.080 mole) was added 40 ml of t-butyl alcohol and di-t-butyl dicarbonate (10.5 g, 0.048 mole). After about 24 h at room temperature the bulk of the t-butyl alcohol was evaporated from the reaction mixture and the resulting aqueous phase was washed once with diethyl ether. The aqueous layer was acidified to pH 2.0 with 2N HCl and extracted with ethyl acetate. The extract was dried over MgSO₄ and evaporated to dryness in vacuo. The residue (oil) was dissolved in diethyl ether and dicyclohexylamine, DCHA, (7.9 ml, 0.040 mole) was added to the solution. The solution was allowed to stand for 4 hours at 4° C and the salt which had precipitated was filtered, washed with diethyl ether and dried under vacuum to give 15.7 g (86% yield) of the pure DCHA salt 2.

FD-MS 459 (MH+). Elemental analysis for C₂₇H₄₂N₂O₄: Theory: C, 70.71; H, 9.23; N, 6.11. Found: C, 71.07; H, 9.37; N, 5.87.

3) t-Butyloxycarbonyl-DL-1,2,3,4-tetrahydroisoquinolin-1-ozlazetidine-2-carboxylic acid. (Boc-DL-1-Tiq-Azt-OH)

The DCHA salt(2) (13.7 g, 30 mmole) was suspended in 200 ml of ethyl acetate and the suspension washed with 1.5 N citric acid and with water and was dried over Mg SO₄. The suspension was evaporated to dryness under vacuum and the oil residue was dissolved in 100 ml of ethyl acetate. The solution was cooled to 0° C. and 2,4,5-trichlorophenol (5.91 g 30 mmole) was added followed by DCC (6.18 g, 30 mmole). The reaction mixture was stirred for 5 minutes at 0° C. and then warmed to room temperature and stirred for 1.5 h. The reaction mixture was cooled to 0° C, the precipitate filtered and the mother liquor evaporated to dryness in vacuo. The oil residue was dissolved in 80 ml of pyridine and 2-azetidine-2-carboxylic acid (3.0 g, 30 mmole) and 4.2 ml (30 mmole) of triethylamine were added to the solution. The reaction mixture was stirred for 48 h at room temperature and was evaporated to dryness under vacuum. The residue was dissolved in ethyl acetate/water and the pH of the solution was adjusted to 9.5 with 2N sodium hydroxide. The aqueous layer was separated, acidified to pH 2.0 with 2N HCl and then extracted with ethyl acetate. The extract was dried over MgSO₄ and evaporated to dryness in vacuo to give 10 g of 3.

The product (3) was dissolved in chloroform:hexane (1:1, v:v) and the solution appliedc to a silica gel column equilibrated in hexane in a Water's Prep 500A. The product (3) was eluted with a gradient of increasing concentrations of ethyl acetate. Fractions were collected and the product isolated based on TLC profile. Fractions were combined and evaporated to dryness to give 4.8 g (44% yield) of pure 3.

TLC R$_f$ (A) 0.35. FAB-MS 361 (MH+). [α]D = −20.6° C. = 0.5 CH₃OH.

4)
t-Butyloxycarbonyl-DL-1,2,3,4-tetrahydro-1-isoquinolinoyl-L-azetidinyl-L-arginine(Cbz)lactam(4)
(Boc-DL-1-Tiq-Azt-Arg(Z)-Lactam)

In a first flask Boc-DL-1-Tiq-Azt (3) (5.3 g, 15 mmole) was dissolved in 50 ml of DMF and the solution cooled to −15° C. N-Methylmorpholine (1.65 ml, 15 mmole) and the reaction mixture was stirred at −15° C. for two minutes.

In a second flask Arg(Z)-Lactam as the trifluoroacelate salt (TFA) (6.06 g, 15 mmole) was dissolved in 20 ml of DMF and the solution cooled to 0° C. N- Methylmorpholine (1.98 ml, 19 mmole) was added to the cold solution which was stirred for 2 min at 0° C. Then the contents of the second flask were poured into the first flask and the reaction mixture was stirred at −15° C. for 3 h. The mixture was slowly warmed to room temperature overnight and was then evaporated to an oil in vacuo. Ethyl acetate (175 ml) and 1N NaHCO₃ (100 ml) were added to the oil. The organic layer was separated, washed with water, 1.5N citric acid, and again with water. The solution was dried over Mg SO₄ and evaporated to dryness under vacuum to give 6.9 g (73% yield) of 4,Boc-DL-1-Tiq-Azt(Z)-Lactam as an amorphorous solid.

TLC R$_f$(A) 0.64. FAB-MS 633 (MH+). [α]D −62.5° C. C=0.5 CHCl₃.

5) Boc-DL-1-Tiq-Azt-Arg(Z)-H(5)

A solution of Boc-DL-1-Tiq-Azt-Arg(Z)-Lactam(4) (6.3 g, 10 mmole) in 85 ml if dry THF was cooled in an atmosphere of nitrogen to −15° C. and lithium aluminum hydride, 1M in THF (10 ml, 10 mmole) was added dropwise over 30 min. After addition of the hydride was complete, the reaction mixture was stirred for 30 min. at −15° C. Next, a solution of 10 ml of THF and 3.0 ml of 0.5N H₂SO₄ was added dropwise to the reaction mixture over 5 min. The mixture was diluted with 200 ml of ethyl acetate and 200 ml of water, the organic layer separated, dried over Mg SO₄ and evaporated to dryness under vacuum to give 6.0 g (95% yield) of 5 as an amorphous solid.

TLC R$_f$(A) 0.18.

6) DL-1-Tiq-Azt-ARg-H sulfate

To a solution of (5) (5.9 g, 9.3 mmole) in 60 ml of THF and 30 ml of water were added 10 ml of 1N H₂SO₄ and 2.0 g of 5% Pd/c catalyst. Nitrogen was bubbled through the suspension with a gas dispersion tube for 5 minutes followed by hydrogen for 1.5 h and again with nitrogen for 5 min. The catalyst was filtered and the pH of the filtrate was adjusted to pH 4.0 with Bio-Rad AG1-X8 resin (hydroxide form). The resin was filtered and the filtrate freeze dried to give 4.5 g of dry solid. The solid was treated for 10 minutes at 0° C. with 20 ml of trifluoroacetic acid and 5 ml of anisole. The reaction mixture was stirred for 10 min and then evaporated without heat. Diethyl ether (100 ml) was added to the concentrate and the precipitate which formed was collected and dried to give 4.8 g of the crude product.

EXAMPLE 2

DL-1,2,3,4-tetrahydroisoquinolin-1-oyl-L-azetidinyl-L-arginine aldehyde sulfate purification The crude product (4.8 g) of Preparation 2 was dissolved in 0.01% H₂SO₄ and applied to two 5×25 cm Vydac C₁₈ resin columns connected in series. A gradient of increasing concentration of acetonitrile (2% to 25%) was used to elute the peptide salt from the column. Fractions were collected and pooled on the basis of analytical RP-HPLC described hereinabove. The pH of the pooled fractions were adjusted to pH 4.0 using AG1-X8 resin (Bio Rad anion exchange resin, 50–100 mesh) in hydroxide form. The resin was filtered and the filtrate lyophilized to give 1.36 g (30% yield) of the purified title sulfate salt.

FAB-MS 401 (MH+). HPLC Retention Time: 23.1 min.

I claim:

1. A method for purifying a compound of the formulae

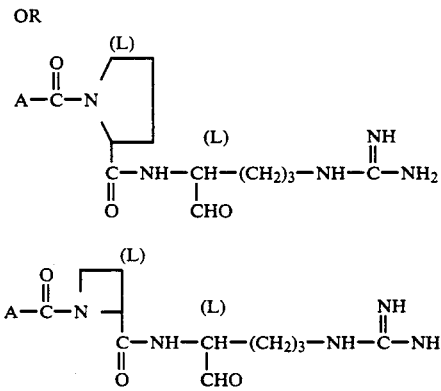

which comprises chromatographing said compound on a reversed phase high pressure liquid chromatogram by gradient elution with a gradient comprising an organic phase of about 2% to about 40% by volume of eluant of acetonitrile in an aqueous phase comprising a dilute sulfuric acid at a pH between about 2 and about 3; adjusting the pH of the eluate to about 4 to about 6.5 with a water insoluble basic resin; separating the resin from the eluate; and, removing the water from the eluate; wherein A is 1) a group of the formula

wherein R is a phenyl group of the formula

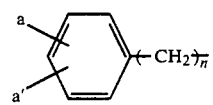

wherein a and a' independently are hydrogen, lower alkyl, lower alkoxy, halogen, trifluoromethyl, hydroxy, hydroxymethyl, amino, or aminomethyl; and n is 0 or 1; or R is thienyl, furyl, naphtyl, or naphthyl mono- or disubstituted by lower alkyl, lower alkoxy, halogen, amino, mono- or di-(lower alkyl)amino, or hydroxy; or R is cyclohexadienyl, cyclohexenyl, cyclohexyl or cyclopentyl;

$R_1$ is hydrogen, methyl or ethyl;

B is lower alkyl, lower alkoxy, hydroxy, or an amino group of the formula

—N($R_2$)($R_3$)

wherein $R_2$ and $R_3$ independently are hydrogen or lower alkyl, or $R_2$ is hydrogen, and $R_3$ is $C_1$-$C_6$ alkanoyl, halo substituted $C_2$-$C_6$ alkanoyl, or an oxycarbonyl group of the formula $R_4$—OC(O)— wherein $R_4$ is $C_1$-$C_6$ alkenyl, $C_3$-$C_7$ cycloalkyl, benzyl, nitrobenzyl, diphenylmethyl, or a phenyl group as defined above; provided, that when $R_1$ is methyl or ethyl, B is other than methyl or ethyl; 2) a bicyclic group of the formula 3

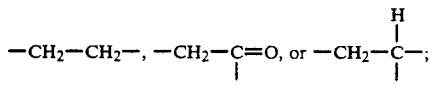

wherein

Q is a one carbon radical represented by

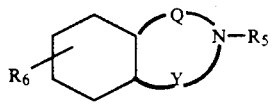

or a two carbon radical represented by

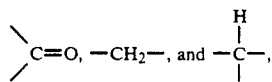

Y is a one carbon radical represented by

or a two carbon radical represented by

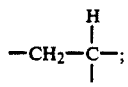

provided that one, but not both, of Q and Y is

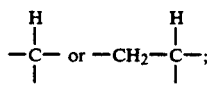

and, provided further, that only one of Q and Y is a two carbon radical;

$R_5$ is hydrogen or an oxycarbonyl group, $R_4$—OC(O)—, as defined above; and $R_6$ is hydrogen, lower alkyl, lower alkoxy, halogen, hydroxy, trifluoromethyl, carboxy, carbamoyl, or aminosulfonyl; and the dotted circle within the 6-membered ring indicates an aromatic ring or a perhydro ring;

and the salts thereof formed with sulfuric acid.

2. The method of claim 1 wherein A is a group of the formula (R)($R_1$)(B)C—.

3. The method of claim 1 wherein A is a bicyclic group of the formula

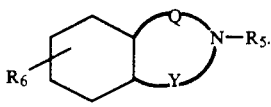

4. The method of claim 3 wherein A is D-1,2,3,4-tetrahydroquinolin-1-yl.

5. The method of claim 3 wherein D-1,2,3,4-tetrahydroisoquinolin-1-oyl-1-prolyl-L-arginine aldehyde sulfate is chromatographed.

6. The method of claim 2 wherein N-methyl-D-phenylalanyl-L-prolyl-L-arginine aldehyde sulfate is chromatographed.

7. The method of claim 3 wherein said compound is N-(D-decahydroisoquinolin-1-oyl)-L-prolyl-L-arginine aldehyde.

8. The method of claim 3 wherein said compound is N-(D-decahydroisoquinolin-3-oyl)-L-prolyl-L-arginine aldehyde.

* * * * *

UNITED STATES PATENT AND TRADEMARK OFFICE
CERTIFICATE OF CORRECTION

PATENT NO. : 5,250,660
DATED : Oct. 5, 1993
INVENTOR(S) : Robert T. Shuman

It is certified that error appears in the above-indentified patent and that said Letters Patent is hereby corrected as shown below:

Column 14, line 29, delete "or" and insert -- or -- in line 37 between structures 1 and 2.

Column 15, line 26, after "wherein $R_4$ is", insert -- $C_1$-$C_6$ alkyl,--.

Column 15, line 26, "$C_1$-$C_6$ alkenyl", should read -- $C_2$-$C_6$ alkenyl --.

Column 15, line 35, (the structure) a dotted circle should be within the 6-membered ring.

Column 15, line 55, after the phrase "represented by", insert -- -$CH_2$-, or --.

Column 16, in the structure in Claim 3, a dotted circle should be within the 6-membered ring.

Signed and Sealed this

Twenty-sixth Day of July, 1994

Attest:

BRUCE LEHMAN

*Attesting Officer*   *Commissioner of Patents and Trademarks*